(12) United States Patent
Ebnet

(10) Patent No.: US 11,969,561 B2
(45) Date of Patent: Apr. 30, 2024

(54) FIXING DEVICE

(71) Applicant: EBNET MEDICAL GMBH, Schwerin (DE)

(72) Inventor: Jens Ebnet, Schwerin (DE)

(73) Assignee: EBNET MEDICAL GMBH, Schwerin (DE)

( * ) Notice: Subject to any disclaimer, the term of this patent is extended or adjusted under 35 U.S.C. 154(b) by 140 days.

(21) Appl. No.: 17/270,180

(22) PCT Filed: Aug. 21, 2019

(86) PCT No.: PCT/EP2019/072372
§ 371 (c)(1),
(2) Date: Feb. 22, 2021

(87) PCT Pub. No.: WO2020/038997
PCT Pub. Date: Feb. 27, 2020

(65) Prior Publication Data
US 2021/0244918 A1  Aug. 12, 2021

(30) Foreign Application Priority Data
Aug. 23, 2018 (DE) ............... 10 2018 120 585.6

(51) Int. Cl.
*A61M 25/02* (2006.01)
*A61M 5/14* (2006.01)
*A61M 5/32* (2006.01)

(52) U.S. Cl.
CPC ..... *A61M 25/02* (2013.01); *A61M 2005/1416* (2013.01); *A61M 2005/3289* (2013.01);
(Continued)

(58) Field of Classification Search
CPC .......... A61M 25/02; A61M 2025/0246; A61M 2025/026; A61M 2025/028;
(Continued)

(56) References Cited

U.S. PATENT DOCUMENTS 9,993,620 B2 * 6/2018 Le .................. A61M 25/02
2001/0056261 A1 12/2001 Lerman et al.
(Continued)

FOREIGN PATENT DOCUMENTS

EP      1 852 140 A1   11/2007
WO    2005/102425 A2   11/2005
(Continued)

*Primary Examiner* — William R Carpenter
*Assistant Examiner* — Robert F Allen
(74) *Attorney, Agent, or Firm* — WCF IP

(57) ABSTRACT

The invention relates to a fixing device for fixing a medical, cosmetic, decorative or other article to the skin of a living being, the fixing device comprising the following features: a) a first retaining element having a first piercing point, which is designed to pierce the skin, b) a second retaining element having a second piercing point, which is designed to pierce the skin, the second piercing point being arranged at a distance from the first piercing point, c) a bridge, to which the first and the second retaining element are fastened, d) a fixing portion, which is connected to the bridge or is part of the bridge, the fixing portion being designed to fix the article that is to be fixed.

14 Claims, 3 Drawing Sheets

(52) U.S. Cl.
CPC ........... *A61M 2025/0213* (2013.01); *A61M 2025/0233* (2013.01); *A61M 2025/024* (2013.01); *A61M 2025/0246* (2013.01); *A61M 2025/026* (2013.01); *A61M 2025/028* (2013.01); *A61M 2025/0286* (2013.01); *A61M 2025/0293* (2013.01)

(58) Field of Classification Search
CPC ........ A61M 2025/0286; A61M 5/1418; A61M 2025/024; A61M 2005/1416; A61M 2005/3289; A61M 2025/0213; A61M 2025/0233; A61M 2025/0293; A61B 2017/0645; A61B 17/0644; A61B 17/064; A61B 17/076; A61B 2017/081; A61B 17/083; A61B 2017/088; A61B 17/122; A61B 17/0057; A61B 2017/00584; A61B 2017/00668
See application file for complete search history.

(56) References Cited

U.S. PATENT DOCUMENTS

| | | | |
|---|---|---|---|
| 2005/0256459 A1* | 11/2005 | Howard | A61M 25/02 604/174 |
| 2010/0145280 A1 | 6/2010 | Daniels, Jr. et al. | |
| 2015/0005733 A1* | 1/2015 | Le | A61M 25/02 604/174 |

FOREIGN PATENT DOCUMENTS

| | | |
|---|---|---|
| WO | 2007/082333 A1 | 7/2007 |
| WO | 2016/138037 A1 | 9/2016 |

* cited by examiner

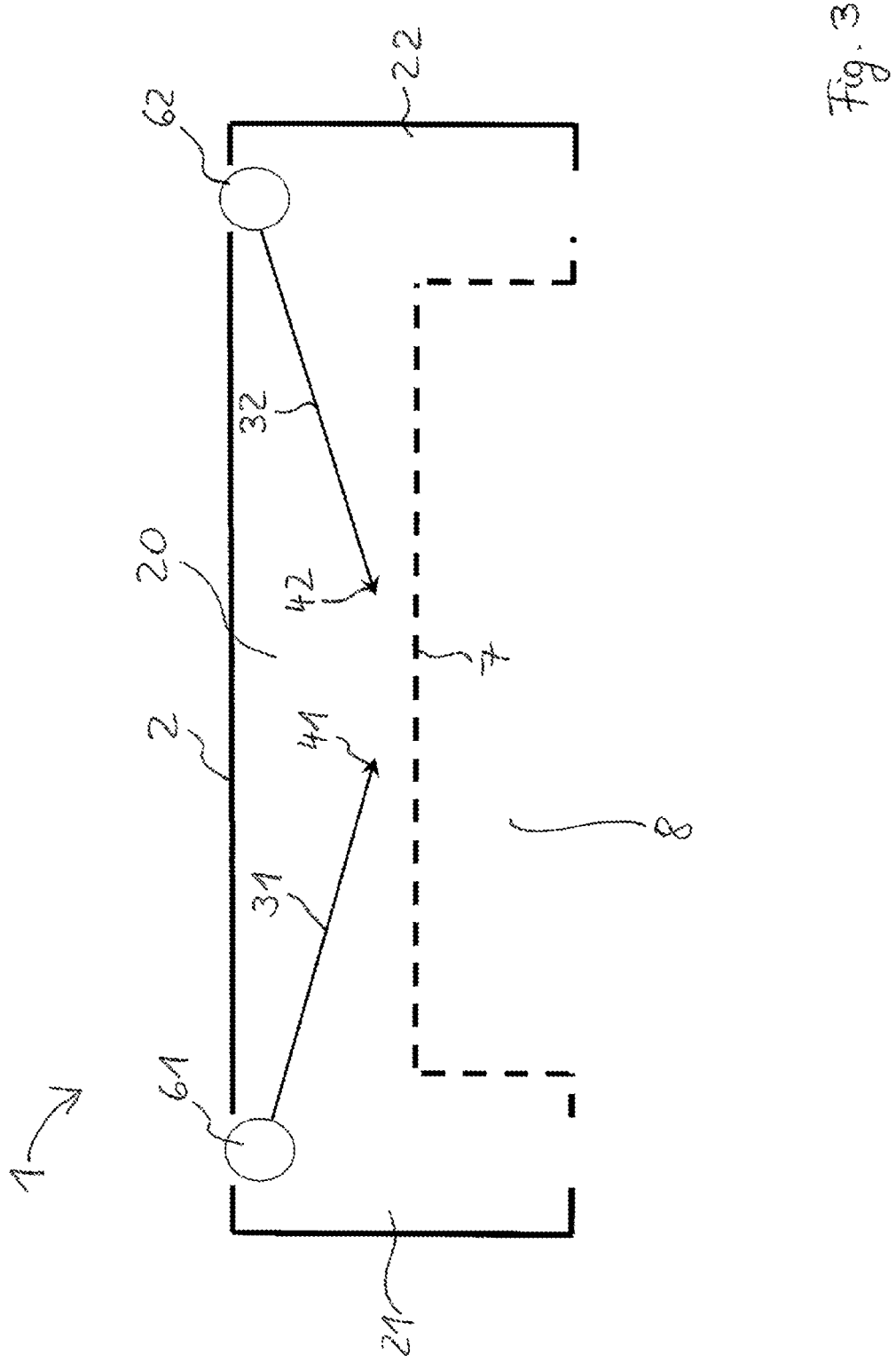

FIXING DEVICE

The invention relates to a fixing device for fixing a medical, cosmetic, decorative or other article to the skin of a living being. An important field of use of the fixing device according to the invention is in the medical sector, for example for fixing catheters, tubes and drains (hereinafter only "catheters") or parts thereof to the skin or to other anatomical structures (hereinafter only "skin") of a living being. Where the word "patient" is used in the following, this means explicitly both a patient in the field of human medicine and one in the field of veterinary medicine, that is to say a living being in the broadest sense.

Catheters, which are inserted through the skin and the subcutaneous connective tissue into the target structures of a body, have to be regularly fixed to the skin so that they do not slip out of the target structure or the body. A variety of influences makes this fixing difficult, of which some examples are: sweat and secretion production by the skin, escape of liquid at the piercing site, the need for skin care. The fixing of catheters to the skin, for example especially also vascular catheters, therefore represents a particular challenge.

In practice, the challenge is mainly overcome by suturing the catheters to the skin. Further fixing is generally provided by plasters, which additionally have the function of providing a sterile covering of the piercing site or of the entry point of the catheter into the skin. Fixing by plasters or also by dressing material alone is usually insufficient.

The suturing of catheters is associated with a number of disadvantages and dangers to the patient and user. For example, when fixing a catheter with a suture, there is always the danger of the needle and thread penetrating too deeply into the body and, for example, hitting a blood vessel. This commonly occurs in practice and is manifested, for example, by an immediate escape of blood from the skin along the suture and/or by the formation of a bruise near the suture site.

In addition, the suturing or knotting technique has to be learned and practiced: tied knots can come undone and loosen. Moreover, the suture or the knot must be neither too tight (possible reduced blood flow to the skin region due to compression of small blood vessels) nor too loose (insufficient fixing of the catheter in the desired position). There is a considerable outlay in terms of material, since the needle, thread, and possibly instruments such as a needle holder for guiding the needle and a scalpel for severing the thread after the suturing, must be provided in a sterile state. In addition, the choice of the appropriate thread is not a trivial one, since the thread must not break down in the living being.

The threads must be easy to remove after the catheter is withdrawn. Moreover, it is sometimes necessary for the position of the catheter to be changed (e.g. drawn back) in a controlled manner after it has been put in place. This may require removal of stitches and renewed suturing. The suturing (sometimes also the removal of stitches) is also painful when the patient is conscious. In addition, a fixing procedure requires the needle to be passed in and out of the skin, and this often requires local anesthetic.

Moreover, the passage of the needle in and out of the skin always results in the formation of at least two ports of entry for microorganisms into the body. The thread can in this case also serve as a kind of "guide rail" for the admission of microorganisms. This is of practical importance in the case of patients who are seriously ill or whose immune systems are weakened. Not least, the user may suffer a needlestick injury during the suturing procedure and, for example, become infected with a potentially life-threatening viral disease. The patient too may suffer a needlestick injury.

The object of the invention is therefore to improve the fixing of such articles to the skin of a living being in order to avoid the aforementioned disadvantages.

This object is achieved by a fixing device for fixing a medical, cosmetic, decorative or other article to the skin of a living being, the fixing device having the following features:

a) a first retaining element having a first piercing tip, which is designed to pierce the skin,
b) a second retaining element having a second piercing tip, which is designed to pierce the skin, the second piercing tip being arranged at a distance from the first piercing tip,
c) a bridge, to which the first and the second retaining element are fastened,
d) a fixing portion, which is connected to the bridge or is part of the bridge, the fixing portion being designed for fixing the article that is to be fixed.

The fixing device according to the invention is distinguished by its ease of handling by the user. The first and the second piercing tip permit minimally invasive fixing of the article that is to be fixed to the skin of the living being. The fixing device according to the invention can also be produced easily and cost-effectively and can accordingly be made available as an inexpensive mass-produced item. The fixing device according to the invention is of great practical relevance, since it can greatly improve patient care and can greatly increase the safety of patient and user. It may be assumed that there is a considerable medical need for this.

The fixing device can in this way be fixed releasably to the skin via the first and the second piercing tip. To ensure that the first and the second piercing tip do not come loose in an undesirable way after penetrating the skin, the first and the second piercing tip can be suitably prepared, for example by means of the first and the second piercing tip being angled slightly inward such that they point toward each other. The fixing in the skin is improved in this way. Alternatively or additionally, the first and the second piercing tip can have one or more small barbs which can be removed from the skin again without causing any appreciable injury. The barbs can moreover be designed as foldable barbs which, when the fixing device is pulled with suitable force, are released again from the skin by means of automatically unfolding under the effect of the pulling action. A further possibility is to design the first and the second piercing tip with increased frictional resistance, for example by selection of a material with increased friction or by roughening or other suitable finishing of the surface.

The fixing portion can be designed, for example, simply as one surface side of the bridge. The fixing portion can also have a defined configuration which is adapted to the outer shape of the article that is to be fixed, for example a semicircular shape or a clip shape. The fixing portion can be made wholly or partially of a material that can be modeled and that wholly or partially adapts to the shape of the article that is to be fixed, e.g. when the fixing device according to the invention is placed on the article that is to be fixed. The fixing portion can moreover be designed with increased frictional resistance, for example by selection of a material with increased friction or by roughening or other suitable finishing of the surface. The surface can also have a special structure, e.g. a structure with dimples or grooves or a zipper-like structure. The surface can also have adhesive properties or can be coated with an adhesive material. The surface coating can also be a nanocoating, which forms a nanostructured surface. The fixing portion can also have properties akin to a suction cup and can use a vacuum mechanism to fix the article that is to be fixed. It is also possible that a plastic or rubber element having properties akin to a suction cup is placed on the fixing portion. Similarly, a plurality of these elements can be placed on the fixing portion.

According to an advantageous embodiment of the invention, provision is made that the fixing device has at least one basic state, in which the fixing device is made available by the manufacturer (delivery state of the fixing device) or which is present at least before the first use of the fixing device for fixing the article to the skin, and at least one use state, which is different from the basic state and which is present at least during fixing of the fixing device to the skin. In the use state, the fixing device can differ from the basic state in that, for example, it has another outer shape, or individual elements of the fixing device are differently positioned. For example, in the use state, the first and the second retaining element can be arranged on the bridge in a different way than in the basic state. It is thus possible to realize different functionalities of the fixing device depending on the adopted state.

According to an advantageous embodiment of the invention, provision is made that the first and the second retaining element, at least in the basic state and/or at least in the use state, are arranged substantially parallel to each other. The first and the second retaining element can also be at a slight angle to each other, in which case it is advantageous if this angle is at least smaller than 10 degrees. It is in this way possible to fix the fixing device to the skin by simply applying pressure, with the first and the second piercing tip leading at the front. The first and the second piercing tip penetrate the surface of the skin without difficulty and can in this way be anchored in the skin.

According to an advantageous embodiment of the invention, provision is made that the fixing device has a protective mechanism by which, at least in the basic state, the first and the second piercing tip are protected against being touched. This has the advantage that, during the unpacking of the fixing device and during initial handling of the fixing device, the user and also other persons are protected against accidental injuries caused by the first and the second piercing tip.

According to an advantageous embodiment of the invention, provision is made that the protection provided by the protective mechanism, against touching the first and the second piercing tip, is canceled in the use state. In this way, the fixing device can be reliably fastened to the skin.

According to an advantageous embodiment of the invention, provision is made that the protective mechanism is automatically activatable upon removal of the fixing device from the skin. When the protective mechanism is activated, the protection against touching is made available, i.e. the first and the second piercing tip are then protected against being touched. This has the advantage that no specific action by the user is needed to activate the protective mechanism. In this way, unpredictable and unforeseeable injuries are avoided, in particular even if the fixing device according to the invention should unexpectedly come loose from the patient by accident. For example, the protective mechanism can be activated by spring force.

According to an advantageous embodiment of the invention, provision is made that the fixing device has a final state which is present at least after removal of the fixing device from the skin, wherein, in the final state, the first and the second piercing tip are protected again by the protective mechanism against being touched or are protected by another protective mechanism against being touched. Accidental injuries are avoided in this way too. This can be effected by the aforementioned protective mechanism, or by a further protective mechanism which is present in addition to the protective mechanism first mentioned. In the final state, the fixing device can differ for example from the use state and/or from the basic state. It is also possible that the fixing device in the final state is configured again as in the basic state.

According to an advantageous embodiment of the invention, provision is made that the final state can be automatically adopted upon removal of the fixing device from the skin. This has the advantage that no specific action by the user is needed to activate the protective mechanism. In this way, unpredictable and unforeseeable injuries are avoided.

According to an advantageous embodiment of the invention, provision is made that the protective mechanism has at least one first protective cap which surrounds the first piercing tip in the basic state, and/or the protective mechanism has a second protective cap which surrounds the second piercing tip in the basic state. The first protective cap can also surround further parts of the first retaining element or the whole first retaining element. The second protective cap can also surround further parts of the second retaining element or the whole second retaining element. The first and/or the second protective cap can be designed, for example, as a sleeve-shaped body, for example as a cylindrically shaped body.

According to an advantageous embodiment of the invention, provision is made that the first protective cap is mounted so as to be longitudinally movable relative to the first retaining element, and/or the second protective cap is mounted so as to be longitudinally movable relative to the second retaining element. In this way, the first protective cap is displaceable in the longitudinal direction of the first retaining element. The second protective cap is displaceable in the longitudinal direction relative to the second retaining element. This has the advantage that the respective protective cap can move automatically rearward upon insertion of the piercing tip of a retaining element and thus frees the piercing tip such that the latter can penetrate the skin. The protective cap can be secured on the bridge by a spring arrangement for example, such that, upon deliberate removal of the fixing device from the skin, the protective cap is automatically pushed back by spring force in the direction of the respective piercing tip and again receives this piercing tip in its interior, such that the protection against touching is automatically activated again. Activation of the protection against touching is also of particular importance in a situation where there is an unwanted removal of the fixing device. Should this situation unexpectedly arise, neither the patient nor the user, nor any other living being, can sustain an injury from the fixing device.

According to an advantageous embodiment of the invention, provision is made that the first and/or the second protective cap forms at least one fastening element for fixing the article that is to be fixed. This is possible in particular if the article that is to be fixed has a fixing tab or a fixing wing (hereinafter only "fixing tab"), as is the case with commercially available catheters. With the fixing device in the state fastened to the skin, the respective protective cap can then press against this fixing tab and in this way fix the article that is to be fixed to the skin. This can alternatively or additionally take place with a mechanism which resembles that of a press stud or punch in other fields. The tab-side shape of the respective protective cap can thus vary, e.g. can also be punch-shaped or bead-shaped, in order to increase the surface with which the respective protective cap exerts a pressure on the respective fixing tab. The respective piercing tip can then be guided through a hole that is present anyway in the fixing tab.

According to an advantageous embodiment of the invention, provision is made that the protective mechanism has a spring mechanism formed with at least one spring, wherein the at least one spring has a higher spring pretension in the use state than in the final state. In this way, the protection against touching, provided by the protective mechanism, can be automatically activated by a mechanism of simple design. For example, by means of the spring mechanism, the aforementioned first and/or second protective cap can be automatically extended again and thereby receive the respective piercing tip in its interior. The at least one spring can be curved or straight in the basic state and/or in the use state and/or in the final state. The extension movement of the first and/or second protective cap, which can be generated by the spring mechanism, can be a linear movement, a pivoting movement or a combined linear/pivoting movement. The springs of the spring mechanism can also connect the first and/or the second retaining element to the bridge.

According to an advantageous embodiment of the invention, provision is made that the fixing device has a securing mechanism by which the fixing device is secured in the basic state against direct application in the use state, wherein the securing provided by the securing mechanism has to be canceled by the user in order to bring the fixing device to the use state. In this way, an additional safeguard against incorrect use of the fixing device is created. The user first has to deliberately cancel the securing provided by securing mechanism, otherwise he cannot use the fixing device to fix the article that is to be fixed to the skin.

According to an advantageous embodiment of the invention, provision is made that the fixing portion is arranged on that side of the bridge facing toward the first and the second piercing tip. In this way, the article that is to be fixed can be received between the first and the second retaining element and the bridge and can in this way be held on the skin by means of the bridge or by the fixing portion.

According to an advantageous embodiment of the invention, provision is made that the fixing device has a receiving space between the first and the second retaining element, for receiving the article that is to be fixed. The receiving space can be likewise arranged, for example, on the bridge facing toward the first and the second piercing tip.

According to an advantageous embodiment of the invention, provision is made that the fixing device or its bridge is arch-shaped and/or U-shaped or inverted U-shaped. This permits simple and cost-effective production of the fixing device, or of its bridge, and also a robust design of the fixing device.

According to an advantageous embodiment of the invention, provision is made that the first and/or the second retaining element are mounted so as to be pivotable and/or longitudinally displaceable relative to the bridge. For example, in the final state, so as to form protection against touching, the first and/or the second retaining element can be driven in the longitudinal direction into the bridge or can be swiveled into the bridge by a pivoting movement. In this way, the bridge then forms a protection against touching, for example in the sense of the aforementioned further protective mechanism.

The invention affords the following further advantages:

The fixing device according to the invention makes fixing catheters to the skin much easier, quicker, safer and more cost-effective.

The design of the fixing device according to the invention is based on the medical experience of the inventor and is of great relevance in practice.

It is simple to use. The fixing device according to the invention can be operated intuitively; all of the components can be structurally integrated.

It is quick to use. Use under pressure of time and in emergency situations is possible.

It is safe to use. The danger of an additional injury to user and patient (needlestick injury) is minimal or even eliminated.

It is cost-effective to use. The fixing device according to the invention can be made available as a mass-produced item. Its use is therefore also advantageous from the financial point of view.

The fixing device according to the invention securely fastens the article that is to be fixed even under difficult circumstances but can be quickly released again when necessary.

The fixing device affords the advantage that the contact pressure with which the fixing device fixes the article that is to be fixed can be predefined within narrow limits. In this way, for example, there is less danger of a reduced blood flow to the skin region beneath the article that is to be fixed. Since the article that is to be fixed is not pressed with too great a force onto the skin, small blood vessels are not appreciably compressed, and the flow of blood to the skin is thus maintained.

Hygiene aspects can be taken into account. The fixing device according to the invention can be designed, for example, as a product that is to be used just once.

The fixing device according to the invention is compatible with customary catheters and also with recently developed catheters such as the Swordcath®.

The fixing device according to the invention can already be a constituent part of a catheter or can be applied as an individual element to the catheter.

A variable length of the retaining elements permits optimum use in different subgroups of living beings. For example, the retaining elements for use in smaller living beings can be made shorter. The length of the retaining elements can in particular also be adapted to use in different anatomical regions of a living being.

Customary catheters often already have holes for suturing. These holes are punched out on fixing tabs, which protrude from the catheter to right and left ("fixing wings"). The fixing device according to the invention is compatible with these and is optimally adapted to the components of existing catheters.

The entire fixing device or at least parts thereof, for example only the bridge, can be made of antibacterial and/or antimicrobial material or can be coated with such a material. The entire fixing device or at least parts thereof can be made of a material compatible with MRT/nuclear magnetic resonance tomography. The first and the second retaining element can in particular be made of a different material than the bridge. The bridge can be made, for example, of a plastic material, in particular a hard plastic. The first and the second retaining element can be made of metal or of another material, for example likewise of a hard plastic. It is also possible that the first and the second retaining element are made of a resorbable material which, through contact with the body, is wholly or partially broken down or dissolved within a defined time period. The material from which the first and the second retaining element are made can moreover have thermoplastic properties and/or properties that change according to the environment. Thus, the material used can, through contact with the body, assume properties different than those when it is located outside the body. For example, the material can have an increased frictional resistance or adhesive properties as soon as it comes into contact with the body. For example, the material can also change in shape as soon as it comes into contact with the body. It is advantageous, for example, if the material curves, i.e. has properties like a bimetal, and thus permits anchoring of the retaining elements in the skin and in the subcutaneous connective tissue. It is also advantageous, for example, if the material changes in terms of its diameter, e.g. expands, when it comes into contact with the body. In this way, the retaining elements can be fixed more firmly and more securely in the skin, or they fix themselves by virtue of these material properties. The material can also be provided with a surface coating which, through contact with the body, assumes one of the properties just mentioned. The surface coating can also be a nanocoating, which forms a nanostructured surface. More secure and firmer fixing as described above can be achieved in this way too.

It is particularly advantageous if the entire fixing device, or at least parts thereof, is made of or is coated with an antimicrobial material that repels dirt, blood and water.

By virtue of the configuration according to the invention of the fixing device, it is likewise possible to fasten not only catheters but also other tubes and drains to the skin of the patient. Moreover, it is no longer necessary to shave the skin around the puncture site or around the point of entry of the catheter into the skin. Microlesions, which can serve as ports of entry for microorganisms, are avoided in this way. The clinical significance of the fixing element according to the invention is considerable.

By virtue of the first and the second retaining element, which can be designed as fine skin clips and have a defined position, it is moreover very unlikely for deeper structures beneath the skin to suffer damage. This can indeed happen when catheters are sutured to the skin in the customary manner. By means of the fixing device according to the invention, a catheter can be fixed more easily, more securely, more effectively and more efficiently.

In the context of the present invention, the indefinite article "a" or "an" is not to be understood as meaning a number. For example, if mention is made of a component, this is to be interpreted in the sense of "at least one component". Insofar as angle specifications are given in degrees, they refer to a circular dimension of 360 degrees (360°).

In the fixing device according to the invention, the first and the second retaining element can be arranged substantially parallel to each other in all operating states of the fixing device or at least in one or more operating states, in particular in the basic state and/or in the use state. The first and the second retaining element are arranged so far apart that they cannot touch each other in any operating state of the fixing device.

In this way, it is possible to prevent the retaining elements from damaging each other. The fixing device according to the invention can be composed of structural parts that are formed from different materials. In particular, the first and the second retaining element can be made of or have a different material then the bridge. For example, the first and the second retaining element can be made of metal, while the bridge can be made of a plastic material or another MRT-compatible material. In particular, hard plastic materials can be used, if appropriate with a coating that increases friction.

The first and the second retaining element can likewise be made of a plastic material, e.g. a plastic material mentioned above.

The invention is explained in more detail below on the basis of illustrative embodiments and with reference to the drawings, in which:

FIG. 3 shows a fixing device in the basic state or in the final state.

Figure 1:
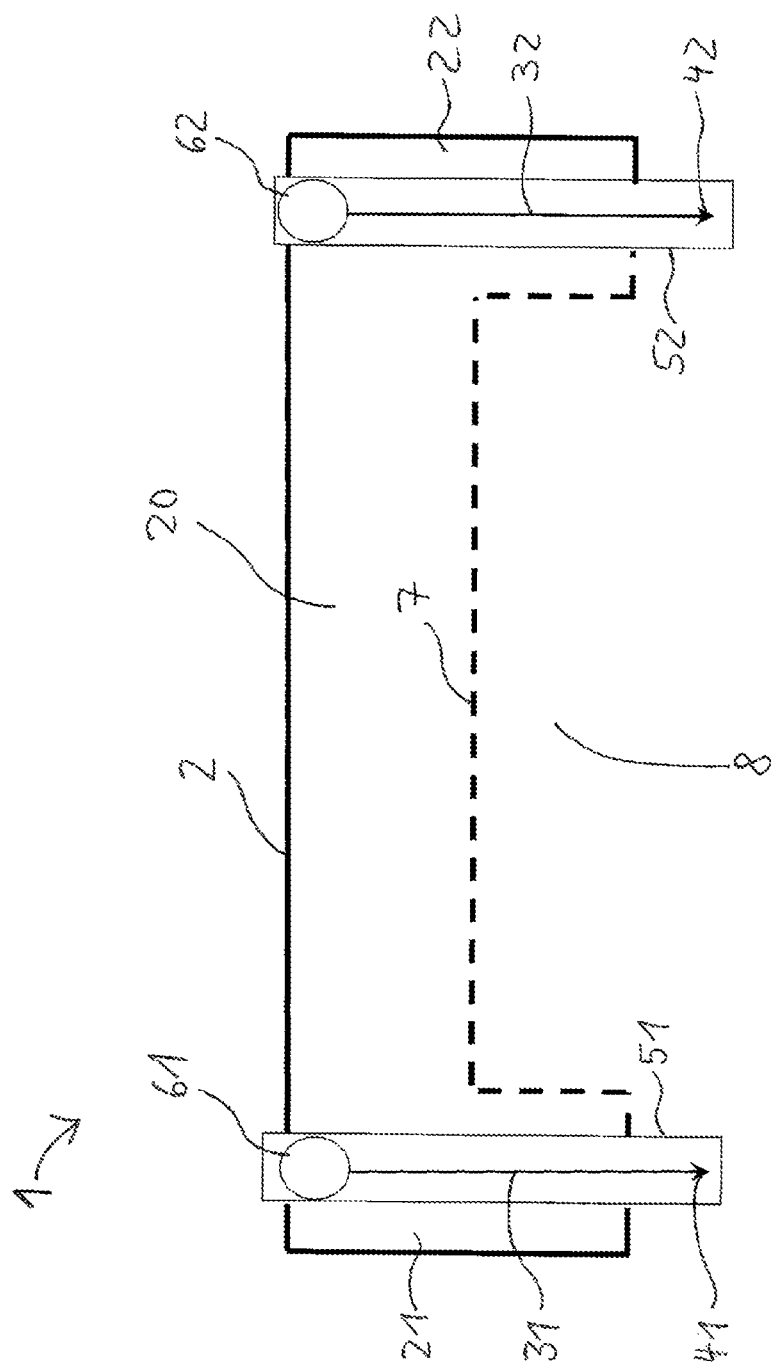
FIG. 1 shows a fixing device in the basic state.

The drawings show the fixing device schematically. The following elements can be seen:

1 fixing device
2 bridge
7 fixing portion
8 receiving space
9 article to be fixed
10 skin
20 central region
21 first side region
22 second side region
31 first retaining element
32 second retaining element
41 first piercing tip
42 second piercing tip
51 first protective cap
52 second protective cap
61 first spring mechanism
62 second spring mechanism
91 first fixing tab
92 second fixing tab FIG. 1 shows the fixing device 1 in the basic state. The final state, adopted after use of the fixing device 1, can in turn correspond here to the basic state. It will be seen that, on the bridge 2, the first protective cap 51 is arranged in a recess in the first side region 21. The first retaining element 31 with the first piercing tip 41 is arranged inside the first protective cap 51. The first protective cap 51 completely surrounds the first piercing tip 41, such that the latter does not protrude outward. The first retaining element 31 is connected to the bridge 2 or the first side region 21 via the first spring mechanism 61. The second protective cap 52 is arranged in a recess in the second side region 22 of the bridge 2. The second retaining element 32 with the second piercing tip 42 is arranged inside the second protective cap 52. The second protective cap 52 completely surrounds the second piercing tip 42, such that the latter does not protrude outward. The second retaining element 32 is connected to the bridge 2 or the second side region 22 via the second spring mechanism 62.

The first side region 21 is connected to the second side region 22 via the central region 20. At the side of the bridge 2 facing toward the first and the second piercing tips 41, 42, the bridge 2 has the fixing portion 7, which is shown with dashed lines. The fixing portion 7 serves for fixing the article 9 that is to be fixed, by means of the article 9 that is to be fixed being received in a receiving space 8 between the first and the second retaining elements 31, 32. The fixing portion 7 can also be designed with a substantially different shape than that shown.

The first protective cap 51 is arranged longitudinally displaceably in the recess of the first side region 21. The second protective cap 52 is arranged longitudinally displaceably in the recess of the second side region 22. This longitudinal displaceability means that, during the use of the fixing device 1, it is possible for the protective caps 51, 52 to be displaced rearward (or upward in the view shown in the figures), such that the piercing tips 41, 42 are exposed. This is shown in FIG. 2.

Figure 2:
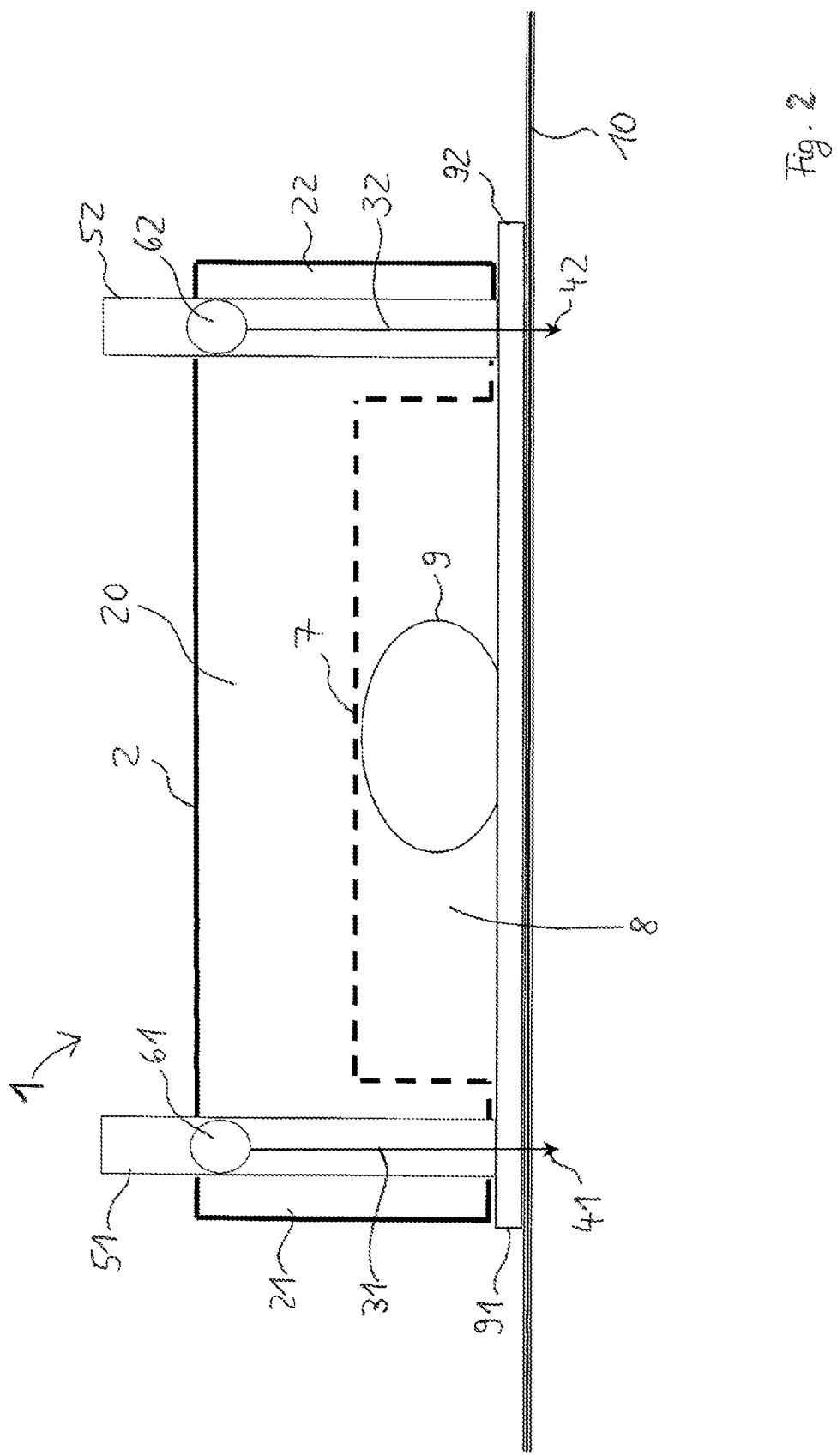
FIG. 2 shows the fixing device according to FIG. 1 in the use state.

In FIG. 2, the fixing device 1 is already fastened to the skin 10 of a living being. As can be seen, the first and the second piercing tips 41, 42 have penetrated the surface of the skin 10 and are anchored therein. The first and the second protective caps 51, 52 are now displaced in an upward direction. The article 9 that is to be fixed is located in the receiving space 8 and is therefore arranged between the skin 10 and the fixing portion 7, for example clamped between them.

If, as is shown in FIG. 2, the article 9 that is to be fixed has a first and a second fixing tab 91, 92, respectively, it is possible to obtain additional fixing to the skin, by means of the first protective cap 51 or the first side region 21 exerting a compressive force on the first fixing tab 91 and/or by means of the second protective cap 52 or the second side region 22 exerting a compressive force on the second fixing tab 92.

When the fixing device 1 is removed again from the skin 10, the protective mechanism is activated again via the first and the second protective caps 51, 52, i.e. the first and the second protective caps 51, 52 move downward again, such that they cover the first and the second piercing tips 41, 42. The fixing device 1 can then look again as it does in FIG. 1.

Alternatively, the fixing device 1 can also be realized without the first protective cap 51 and/or the second protective cap 52, or entirely without a protective mechanism. Alternatively, it is also possible that, in the basic state, protective caps are fitted over the first and the second piercing tips 41, 42, from below as shown in the figures. These protective caps adjoin the first and the second side regions 21, 22 but do not penetrate into the interior of the first and the second side regions 21, 22. Before the fixing device 1 according to the invention is used, these protective caps have to be removed manually by the user.

FIG. 3 shows a further design option for protecting against the first and the second piercing tips 41, 42 being touched. In this case, the first and the second retaining elements 31, 32 are each pivoted toward each other, such that the respective piercing tips 41, 42 is arranged in a cavity present inside the central region 20 of the bridge 2, and in this way the user is protected against touching the piercing tips 41, 42. For this purpose, the fixing portion 7 is designed such it allows the retaining elements 31, 32 to pass through, e.g. by means of the fixing portion 7 having a slit-shaped elongate recess. The retaining elements can fold in or out through this recess. In addition, the side regions 21, 22 are provided with such a recess on their respective side facing toward the fixing portion 7.

The pivoting of the first and the second retaining elements 31, 32 can be effected, for example, via the respective spring mechanism 61, 62, i.e. an automatic pivoting is possible through the spring force of the respective spring mechanism 61, 62. When the fixing device 1 is removed from the skin 10 again, the first retaining element 31 and the second retaining element 32 pivot automatically to the position shown in FIG. 3 under the spring force of the respective spring mechanism.

In the embodiment of FIG. 3, it is possible to do without the protective caps 51, 52. Alternatively, the protective caps 51, 52 can initially be present at least in the basic state, but they can then be removed at least in the final state, which is shown in FIG. 3. The protective caps 51, 52 can be removed by the user, for example, when the use state according to FIG. 2 is adopted.

Alternatively, the view according to FIG. 3 can also represent the basic state of the fixing device 1. This is possible in particular in an embodiment of the fixing device 1 without the protective caps 51, 52. In this case, the fixing device 1 is made available already in the state which is shown in FIG. 3. In this case, the first retaining element 31 and the second retaining element 32 first have to be moved by manual pivoting to the mutually parallel position, as can be seen from FIG. 2, in order then to fasten the fixing device 1 to the skin 10 by piercing the skin by means of the first and the second piercing tips 41, 42. In this way, for example, a securing mechanism can be created for the fixing device 1.

If the fixing device 1 is designed with the protective caps 51, 52 and with the pivotability of the first and the second retaining elements 31, 32, the protective caps 51, 52 can, for example, have recesses (slits) which each extend in the longitudinal direction and through which the respective retaining elements 31, 32 can be pivoted.

Alternatively or additionally, the protective caps 51, 52 can also be arranged to be rotatable about their own longitudinal axes in the recesses of the side regions 21, 22. If the protective caps now have recesses (slits) which each extend in the longitudinal direction and through which the respective retaining element 31, 32 can be pivoted, the latter can then only be pivoted when the recesses (slits) are located in a defined position in the direction of the inner side of the fixing device 1, because the retaining elements 31, 32 automatically tend to pivot inward to the position shown in FIG. 3 through the spring force of the respective spring mechanism 61, 62. By active rotation of the protective caps 51, 52, it is now possible to control whether the position of the retaining elements 31, 32 shown in FIG. 3 is intended to be reached. The corresponding position of the protective caps 51, 52 with respect to their own longitudinal axis can be made visible to the user, for example on the side of the protective caps 51, 52 facing the user, by a graphic marking.

Alternatively or additionally, the effect whereby the retaining elements 31, 32 are pivoted automatically to the position shown in FIG. 3 can already arise upon removal of the protective caps 51, 52. If the protective caps 51, 52 surround the retaining elements 31, 32, they in fact prevent the latter from being pivoted to the position shown in FIG. 3 when the recesses (slits) of the protective caps 51, 52 are either not located in the (inward) direction, in which the spring force of the respective spring mechanism 61, 62 pulls the retaining elements 31, 32, or the protective caps 51, 52 have no recesses (slits) at all. On account of their dimensions, the protective caps 51, 52 themselves cannot be pivoted. When the fixing device 1 is located on an article 9 that is to be fixed, the position of the retaining elements 31, 32, as shown in FIG. 3, is not reached even in the absence of the protective caps 51, 52, since the article 9 to be fixed now lies between the retaining elements 31, 32 and so prevents this. However, since the spring force of the respective spring mechanism 61, 62 causes the retaining elements 31, 32 to tend to the position as shown in FIG. 3, the fixing of the article 9 that is to be fixed in further reinforced. The article 9 that is to be fixed is as it were additionally grasped or clamped by the retaining elements.

For the same reason, however, the automatic activation of the protective mechanism ensures that the protection against touching is also automatically restored if, without being noticed, the fixing device 1 comes loose from the skin of the living being.

The invention claimed is:

1. A fixing device configured for fixing a medical, cosmetic, decorative or other article to skin of a living being, comprising:
   a) a first retaining element having a first piercing tip designed to pierce the skin,
   b) a second retaining element having a second piercing tip designed to pierce the skin, wherein the second piercing tip is arranged at a distance from the first piercing tip,
   c) a bridge comprising an internal cavity, wherein the first retaining element and the second retaining element are each fastened to the bridge,
   d) a fixing portion connected to or which is part of the bridge, wherein the fixing portion is designed for fixing the article that is to be fixed to the skin,
   wherein the first retaining element and the second retaining element are pivotable substantially parallel to each other in a basic state and a use state, and
   wherein the first retaining element and the second retaining element are mounted so as to be pivotable relative to the bridge and toward each other in a protective state,
   wherein the first piercing tip and the second piercing tip are pivotable from a first position outside the internal cavity to a second position in the internal cavity, and
   wherein the distance between the first and second piercing tips is smaller when the first and second piercing tips are in the second position than in the first position.

2. The fixing device as claimed in claim 1, wherein the fixing device has a first protective mechanism by which the first piercing tip and the second piercing tip are protectable against being touched.

3. The fixing device as claimed in claim 2, wherein the fixing device is configured such that protection provided by the first protective mechanism against touching the first piercing tip and the second piercing tip is cancelable.

4. The fixing device as claimed in claim 2, wherein the first protective mechanism is configured to be automatically activatable upon removal of the fixing device from the skin.

5. The fixing device as claimed in claim 2, wherein the fixing device is configured such that the first piercing tip and the second piercing tip are protected by the first protective mechanism against being touched or are protected by a further protective mechanism against being touched after removal of the fixing device from the skin.

6. The fixing device as claimed in claim 5, wherein the fixing device is configured such that protection of the first piercing tip and the second piercing tip is automatically adoptable upon removal of the fixing device from the skin.

7. The fixing device as claimed in claim 5, wherein the first protective mechanism has a spring mechanism formed with at least one spring, wherein the at least one spring has a higher spring pretension when the fixing device is in use than after removal of the fixing device from the skin.

8. The fixing device as claimed in claim 2, wherein the first protective mechanism has a first protective cap which is capable of surrounding the first piercing tip and/or the first protective mechanism has a second protective cap capable of surrounding the second piercing tip.

9. The fixing device as claimed in claim 8, wherein the first protective cap is mounted so as to be longitudinally movable relative to the first retaining element, and/or the second protective cap is mounted so as to be longitudinally movable relative to the second retaining element.

10. The fixing device as claimed in claim 8, wherein the first protective cap and/or the second protective cap forms at least one fastening element for fixing the article that is to be fixed to the skin.

11. The fixing device as claimed in claim 1, wherein the first retaining element and the second retaining element are pivotable toward each other so that the fixing device is secured against direct application to the skin, wherein the first retaining element and the second retaining element must be pivoted away from each other prior to fixing of the fixing device to the skin.

12. The fixing device as claimed in claim 1, wherein the fixing portion is arranged on a side of the bridge facing toward the first piercing tip and the second piercing tip.

13. The fixing device as claimed in claim 1, further comprising a receiving space between the first retaining element and the second retaining element for receiving the article that is to be fixed to the skin.

14. The fixing device as claimed in claim 1, wherein the fixing device or the bridge is arch-shaped and/or U-shaped.

* * * * *